(12) United States Patent
Ichiki et al.

(10) Patent No.: US 6,985,213 B2
(45) Date of Patent: Jan. 10, 2006

(54) METHOD AND APPARATUS FOR MEASURING MATERIAL PROPERTY

(75) Inventors: Masaaki Ichiki, Tsukuba (JP); Koichi Ozaki, Tsukuba (JP); Tokio Kitahara, Tsukuba (JP); Makoto Tanaka, Kashiwa (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 277 days.

(21) Appl. No.: 10/230,148

(22) Filed: Aug. 29, 2002

(65) Prior Publication Data

US 2003/0061883 A1    Apr. 3, 2003

(30) Foreign Application Priority Data

Aug. 29, 2001  (JP) .............................. 2001-260130

(51) Int. Cl.
*G01B 11/16*    (2006.01)

(52) U.S. Cl. .......................................... 356/32; 73/800

(58) Field of Classification Search ......... 356/32–35.5, 356/601–608, 630, 631, 927; 73/788–790, 73/800, 818–825, 862.324, 862.624, 856; 267/140.13, 141

See application file for complete search history.

(56) References Cited

U.S. PATENT DOCUMENTS 4,574,642 A * 3/1986 Fleischman .................. 73/799
4,864,864 A * 9/1989 Yale et al. .................... 73/800
5,517,861 A * 5/1996 Haas et al. ............... 356/237.1

FOREIGN PATENT DOCUMENTS

JP         9-61324       3/1997
JP         2001-59803    3/2001

OTHER PUBLICATIONS

An extract from "Year 2000 Annual Convention Discourse Papers" and the corresponding English translation, vol. II, Aug. 1, 2000.

* cited by examiner

*Primary Examiner*—Zandra V. Smith
*Assistant Examiner*—Juan D. Valentin, II
(74) *Attorney, Agent, or Firm*—Oblon, Spivak, McClelland, Maier & Neustadt, P.C.

(57) ABSTRACT

The present invention provides a method and apparatus mainly for measuring mechanical properties, electrical properties and transducer properties (e.g., electromechanical coupling constant) of piezoelectrics, wherein three measurement specimens of the same material and the same dimension, each having parallel planes, and two insertion plates of the same material and the same dimension, each having known mechanical properties, are stacked alternately, a load is applied to these measurement specimens and insertion plates via the measurement specimens located on both end sides, the displacements in the direction of application of the load are measured before and after application of the load, and an elastic constant of the measurement specimen is determined based on those displacements, and the measurement of the electromechanical coupling constant is applied to the piezoelectrics by using the same apparatus under short-and-open circuit conditions.

11 Claims, 4 Drawing Sheets

METHOD AND APPARATUS FOR MEASURING MATERIAL PROPERTY

TECHNICAL FIELD OF THE INVENTION

The present invention relates to a method and apparatus for precisely measuring a material property of a bulky solid, for example, a transducer which generates electric power based on application of mechanical energy (hereafter referred to as "transducer"), and in particular, it relates to a method and apparatus suitable for measuring a mechanical property and an energy conversion property of a micro-specimen.

DESCRIPTION OF THE RELATED ART

Hitherto, the Young's moduli of members having large dimensions have been determined by calculation based on data of load-strain properties measured with universal testing machines. For example, according to the description of Japanese Unexamined Patent Application Publication No. 2001-59803, a load is applied to a test piece, this is measured using a load cell, and the quantity of displacement is measured with a strain gauge mounted on a measurement block.

However, regarding this method, there is a problem in that adequate precision of displacement measurement cannot be attained in a minute dimension region on the order of micrometers because of the measurement precision of the strain gauge.

According to the description of Japanese Unexamined Patent Application Publication No. 9-61324, a load is applied by a movable jig from both sides of a test piece, while the strain in the loading direction of a test piece and the strain in the direction perpendicular thereto are measured simultaneously with a push-rod displacement gauge and, therefore, the Young's modulus and the Poisson's ratio are measured simultaneously. According to this, it is possible to improve the measurement precision of the Young's modulus in the push-rod displacement gauge method, and in particular, it is significant because measurement in a high-temperature region (1,500° C. or more), at which measurement has been hitherto impossible to perform, has become possible. Consequently, measurement of the coefficient of elasticity, that is an important material datum for designing high-temperature structure equipment used in fields of aerospace, energy, material manufacturing process, etc., can be performed.

However, regarding this method, since the measurement is performed by a displacement gauge method, it is difficult to measure minute dimensional displacements on the order of several micrometers targeted for the present invention.

SUMMARY OF THE INVENTION

It is an object of the present invention to provide a method and apparatus for measuring a material property suitable for measuring and evaluating mechanical properties and energy conversion properties of targets for measurement, wherein the targets primarily include a bulky solid, for example, a transducer used for an electric power generation device which generates electric power from mechanical energy or vibration energy by the use of a mechanical-electrical energy conversion property, especially a decentralized power generation device which is expected to grow in demand in the future.

It is another object of the present invention to provide a method and apparatus for measuring a material property, which has become possible to measure the material property of even a micro-specimen for measurement with precision.

Furthermore, it is another object of the present invention to provide a method and apparatus for measuring a material property, which has become possible to measure a minute dimensional displacement of the measurement specimen with ease and with high precision by a high-precision displacement detection device.

In order to achieve the aforementioned objects, a method for measuring a material property of the present invention includes basically the steps of stacking alternately three measurement specimens of the same material and the same dimension, each having parallel planes, and two insertion plates of the same material and the same dimension, each having known mechanical properties, applying a load to these measurement specimens and insertion plates via the measurement specimens located on both end sides, measuring the displacements in the direction of application of the load before and after application of the load, and determining the elastic constant of the measurement specimen based on those displacements.

In the aforementioned method for measurement, it is appropriate that the displacements in the direction of application of the load before and after application of the load are measured as the displacements of the two insertion plates. In this case, it is effective at measuring with ease and with high precision that the displacements of the two insertion plates are measured with laser displacement gauges which radiate laser light onto the top surface of the upper insertion plate and the undersurface of the lower insertion plate.

In the aforementioned method of the present invention, when an electromechanical coupling constant is determined while the measurement specimen is a bulky solid of a transducer which generates electric power based on application of mechanical energy, the elastic constants of the measurement specimen are measured under the condition that the top surface and the undersurface of the measurement specimen located between the two insertion plates are electrically short-circuited and under the condition that no short-circuit is brought about, and the electromechanical coupling constant of the measurement specimen is determined based on those elastic constants.

In order to achieve the aforementioned objects, an apparatus for measuring a material property of the present invention is provided with two insertion plates of the same material and the same dimension, each having known mechanical properties, to be stacked alternately with three measurement specimens of the same material and the same dimension, each having parallel planes, a load application device for applying a load to these measurement specimens and insertion plates via the measurement specimens located on both end sides, and a displacement measurement device for measuring the displacement in the direction of application of the load before and after application of the load to these measurement specimens and insertion plates.

In the aforementioned apparatus for measuring a material property, it is appropriate that devices, which measure the displacements in the direction of application of the load as the displacements of the two insertion plates, are used for the displacement measurement device. In this case, it is effective at measuring a minute dimensional displacement of the measurement specimen with ease and with high precision that the displacement measurement device for measuring the displacements of the two insertion plates is composed of laser displacement gauges which measure the displacements by radiating laser light onto the top surface of the upper insertion plate and the undersurface of the lower insertion plate.

In the aforementioned apparatus for measurement of the present invention, when an electromechanical coupling constant is determined while the measurement specimen is a bulky solid of a transducer which generates electric power based on application of mechanical energy, it is effective that a circuit for electrically connecting the top surface and the undersurface of the measurement specimen located between the two insertion plates is installed, and a make-and-break switch is installed in the circuit.

According to such a method for measurement and an apparatus therefor of the present invention, by using three measurement specimens of the same material and the same dimension, regarding even a small measurement specimen, measurement of the material properties thereof, for example, the Young's modulus, can be performed with ease and with precision. That is, by using three measurement specimens and alternately stacking them with insertion plates, both sides of the measurement specimen can become in the same contact condition during loading and, therefore, measurement of a minute dimensional displacement on the order of several micrometers can become possible by the use of an equation for calculation.

A material exhibiting piezoelectric phenomenon has a property of performing a function as a transducer which converts electric energy to mechanical energy or, conversely, which converts mechanical energy to electric energy. The electromechanical coupling constant of this material is a basic physical quantity representing a property as an energy transducer, and the square of the magnitude thereof is defined as mechanically accumulated energy in accordance with electrical input energy or electrostatically accumulated energy in accordance with mechanical input energy. This provides a guide for energy conversion. In addition, this has been widely used as the quantity for evaluation of a basic property of a piezoelectric and, in general, this is the quantity attained through measurement with precision electric equipment. However, according to the aforementioned present invention, measurement thereof can be performed with ease by a simple, static measurement apparatus.

In the future, it is expected that the technology for obtaining an electrical output by the use of mechanical energy will grow while being primarily applied to electrical power generation systems for portable electronic equipment and self-contained measurement monitoring equipment. The present invention can be used therefor as a basic means for evaluating properties.

DESCRIPTION OF THE PREFERRED EMBODIMENTS

The embodiments according to the present invention will be described below with reference to the drawings.

Figure 1:
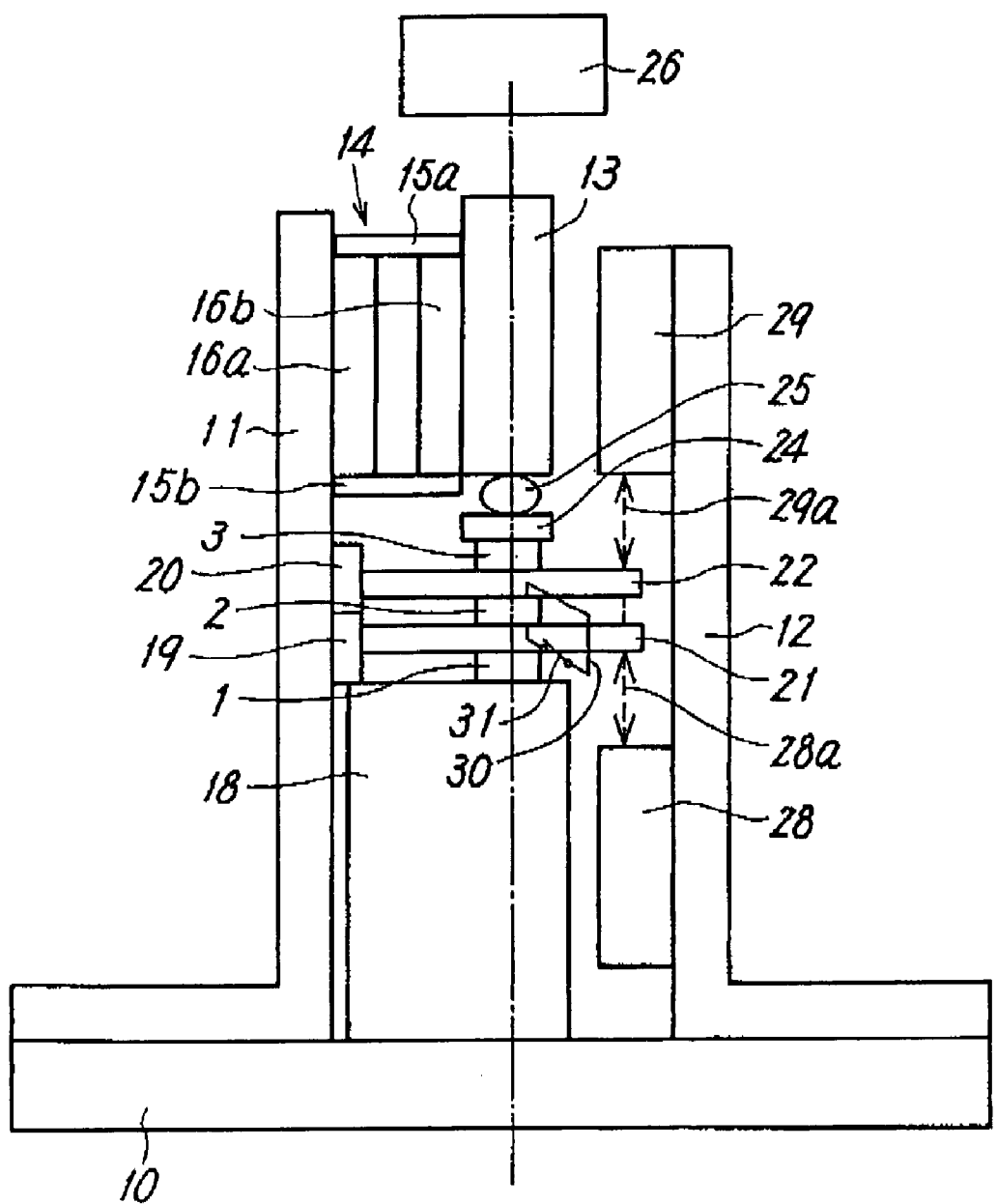
FIG. 1 is a front view showing a basic structure of an evaluation apparatus according to the present invention.

FIG. 1 shows a basic structure of a measurement apparatus main body. In this measurement apparatus main body, a load head mounting column 11 and a sensor mounting column 12 are installed facing each other at an interval required for measurement on a substrate 10. Both end portions of two leaf springs 15a and 15b are connected to each other with joint members 16a and 16b and, therefore, a parallel spring mechanism 14 is configured. The aforementioned one joint member 16a in the parallel spring mechanism 14 is mounted on the aforementioned load head mounting column 11, and a load head 13 is mounted via this parallel spring mechanism 14 while being able to slide in the vertical direction. A sample pedestal 18 is installed below the aforementioned load head 18 on the substrate 10, and positioning jigs 19 and 20 for positioning measurement specimens 1, 2, and 3 placed on the sample pedestal 18 are mounted on the load head mounting column 11 while being free to move up and down.

The measurement specimens 1, 2, and 3 are bulky solid samples to be subjected to measurement of the material property with this measurement apparatus, are made of the same material and the same dimension, and are in the shape of a micro-disk having the size, for example, on the order of 1 to 10 mm $\phi$ in diameter, and having parallel planes. Disk-shaped insertion plates 21 and 22 positioned by the aforementioned positioning jigs 19 and 20 are made of the same material having known mechanical properties, for example, an elastic constant (sometimes called modulus of elasticity, and examples thereof include, for example, Young's modulus, modulus of rigidity, and bulk modulus.), and are formed to have the same dimension. By these insertion plates 21 and 22, the measurement specimens 1, 2, and 3 are positioned in a line while being separated from each other, and are placed on the sample pedestal 18. That is, the measurement specimens and the insertion plates are placed on top surface of the sample pedestal 18 while being stacked alternately in the order of the measurement specimen 1, insertion plate 21, measurement specimen 2, insertion plate 22, and measurement specimen 3 from the bottom. A steel ball 25 is installed between the measurement specimen 3 located at the uppermost position and the load head 13 via an aligning seat 24, and an oil hydraulic press 26 as a load application device is installed on the load head 13.

On the other hand, laser displacement gauges 28 and 29 are mounted as the displacement measurement device, which measure the displacements of the aforementioned measurement specimens and insertion plates in the direction of application of the load as the displacements of the two insertion plates 21 and 22, at the positions facing the insertion plates 21 and 22 on the sensor mounting column 12 while holding the insertion plates 21 and 22 therebetween. The laser displacement gauge 28 radiates laser light 28a onto the undersurface of the insertion plate 21 and, therefore, measures the displacement thereof, and the laser displacement gauge 29 radiates laser light 29a onto the top surface of the insertion plate 22 and, therefore, measures the displacement thereof.

As the displacement measurement devices which measure the displacements of the aforementioned two insertion plates, not only the laser displacement gauge, but also other displacement measurement devices which can measure a minute dimensional displacement with high precision can be used.

A circuit 30 is formed between the top surface and the undersurface of the measurement specimen 2 located at the center in order to electrically connect those surfaces, and a make-and-break switch is installed in the circuit 30.

When the mechanical property of the measurement specimen is measured using the measurement apparatus having the aforementioned configuration, the measurement specimens 1, 2, and 3 and the insertion plates 21 and 22 are set in the condition shown in the drawing, and the oil hydraulic press 26 is driven to apply a force to the load head 13. According to this, the load head 13 pressurizes the measurement specimens 1, 2, and 3 and the insertion plates 21 and 22 placed on the sample pedestal 18 from above via the steel ball 25 and the aligning seat 24.

Figure 2:
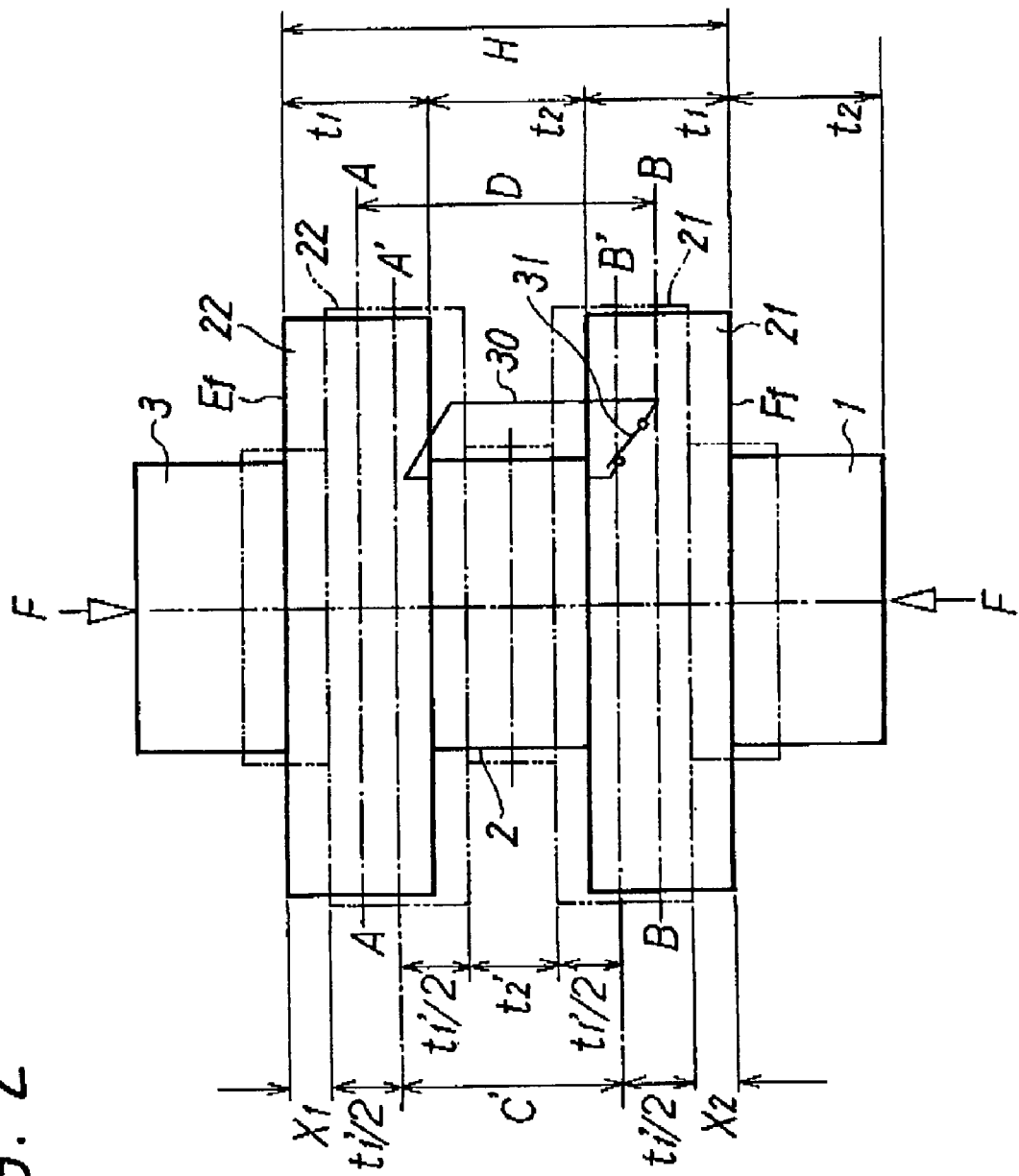
FIG. 2 is a detailed explanation diagram showing the condition that the measurement specimens and the insertion plates shown in FIG. 1 are pressurized.

FIG. 2 represents in detail the condition that the measurement specimens 1, 2, and 3 and the insertion plates 21 and 22 are pressurized.

Herein, the thickness and the Young's modulus of each of the insertion plates 21 and 22 are denoted by $t_1$ and $E_{y1}$, respectively. The thickness and the Young's modulus of each of the measurement specimens 1, 2, and 3 are denoted by $t_2$ and $E_{y2}$, respectively.

The conditions of contact between the measurement specimen 3 and the insertion plate 22, the insertion plate 22 and the measurement specimen 2, the measurement specimen 2 and the insertion plate 21, and the insertion plate 21 and the measurement specimen 1 are assumed to be the same during application of the load. It is assumed that uniformly distributed load is applied to the aforementioned contact portions, and no concentrated stress is generated at the edge portions.

The distance H between the $E_f$ surface of the upper side of the insertion plate 21 and the $F_f$ surface of the lower side of the insertion plate 22 in the unloaded condition is represented by:

$$H = 2t_1 + t_s \quad (1)$$

When it is assumed that the measurement specimens 1, 2, and 3 and the insertion plates 21 and 22 are deformed by a load F brought about by the oil hydraulic press 26 and, therefore, the centerlines A—A and B—B of the insertion plates 21 and 22 are moved to A'—A' and B'—B', respectively, the distance therebetween becomes C', and the thicknesses of the insertion plates 21 and 22 become $t_1'$, the distance H' between the $E_f$ surface and the $F_f$ surface after application of the load is represented by:

$$H' = C' + t_1'/2 + t_1'/2 = C' + t_1' \quad (2)$$

When the thickness of the measurement specimen 2 deformed by the load F is denoted by $t_2'$, since an equation:

$$C' = t_1'/2 + t_1'/2 + t_2' = t_1' + t_2' \quad (3)$$

holds good, the equation (2) becomes $$H' = C' + t_1' = [t_1' + t_2'] + t_1'$$

The difference $\delta(x_1 + x_2)$ between the distance from the $E_f$ surface to the $F_f$ surface before application of the load and that after application of the load is represented by:

$$\delta = H - H' = (2t_1 + t_2) - [[t_1' + t_2'] + t_1'] \quad (4)$$

$$= 2[t_1 - t_1'] + [t_2 - t_2']$$

The quantities of deformation $[t_1-t_1']$ and $[t_2-t_2']$ of the insertion plate 22 (or the insertion plate 21) and the measurement specimen 2, respectively, in the equation (4) are represented by the following equation wherein the contact area is denoted by a and the Young's moduli are denoted by $E_{y1}$ and $E_{y2}$, respectively.

$$[t_1-t_1'] = F/a \cdot t_1/E_{y1} \quad (5)$$

$$[t_2-t_2'] = F/a \cdot t_2/E_{y2} \quad (6)$$

Substitution of the equation (5) and the equation (6) into the equation (4) yields:

$$\delta = 2[F/a \cdot t_1/E_{y1}] + F/a \cdot t_2/E_{y2}$$

$$= F/a[2t_1/E_{y1} + t_2/E_{y2}]$$

By transformation of this equation, the following equation for calculating the Young's modulus $E_{y2}$ of the measurement specimen 2 can be yielded.

$$E_{y2} = t_2/[a\,\delta/F - 2t_1/E_{y1}] \quad (7)$$

Consequently, by measuring the difference $\delta$ between the distance from the $E_f$ surface to the $F_f$ surface before application of the load and that after application of the load with the laser displacement gauges 8 and 17, the Young's modulus $E_{y2}$ of the measurement specimen 2 can be determined.

At that time, by using three measurement specimens as described above, the conditions of contact between the measurement specimen 3 and the insertion plate 22, the insertion plate 22 and the measurement specimen 2, the measurement specimen 2 and the insertion plate 21, and the insertion plate 21 and the measurement specimen 1 can become the same during application of the load and, therefore, the aforementioned equation for calculation holds good. Accordingly, it becomes possible to measure minute dimensional displacements on the order of several micrometers by the use of this equation for calculation.

Figure 3:
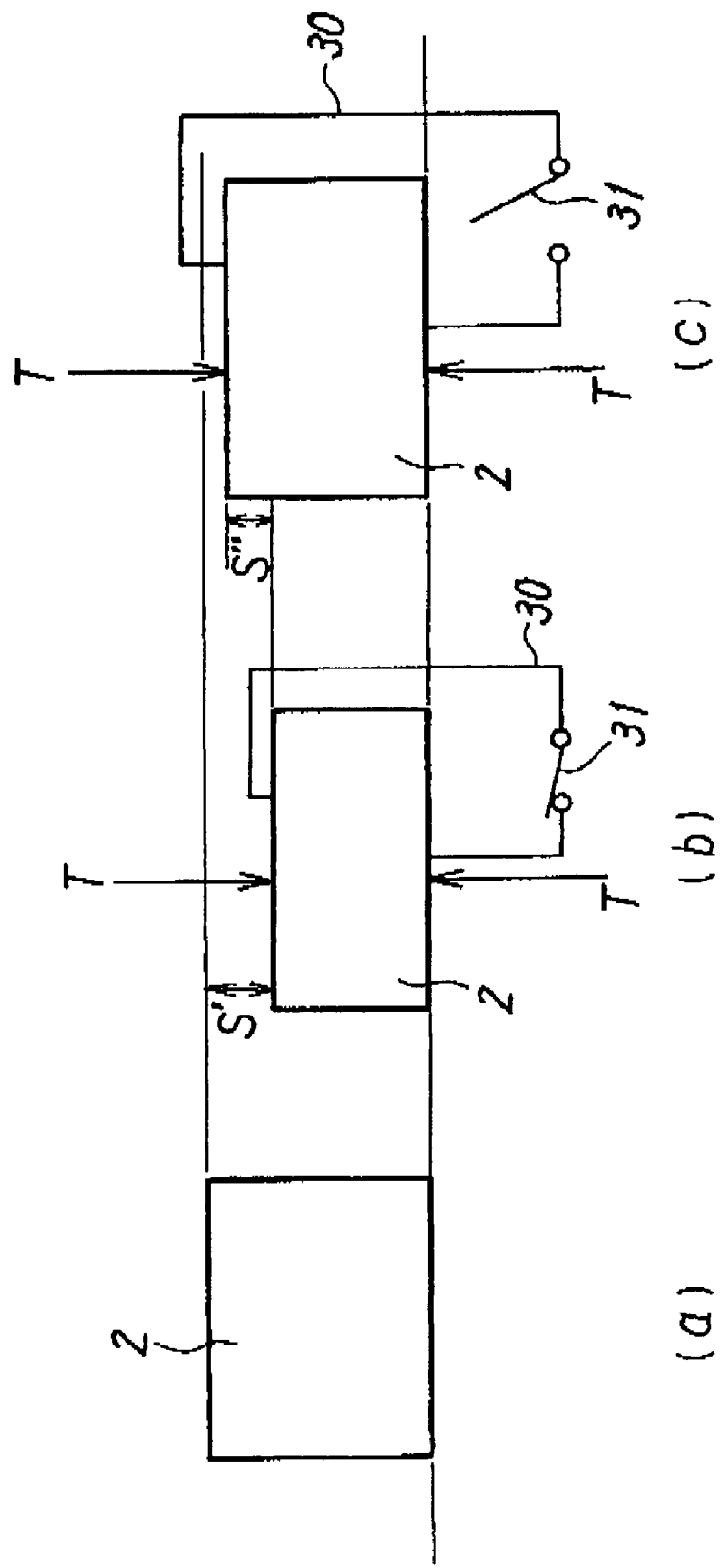
FIG. 3(a) to FIG. 3(c) are explanation diagrams showing the conditions that the elastic constant is measured while both surfaces of a measurement specimen are in the condition of being short-circuited and in the condition of being open-circuit.

In order to measure the energy conversion property of the measurement specimen 2, as shown in FIG. 3(b), a stress is applied to the measurement specimen 2 under the condition that the make-and-break switch 31 in the circuit 30 electrically connecting between the top surface and the undersurface of the measurement specimen 2 is closed, the Young's modulus $s^E$ is measured by the aforementioned method. Thereafter, as shown in FIG. 3(c), a stress is applied to the measurement specimen 2 under the condition that the make-and-break switch 31 is opened, and the Young's modulus $s^D$ is measured by the aforementioned method.

When the measurement specimen 2 is a transducer, the electromechanical coupling constant k that is an energy conversion property can be determined based on the piezoelectric phenomenon as described below.

When strain is denoted by S, stress is denoted by T, electric field is denoted by E, and electric displacement is denoted by D, the basic relationship indicating the piezoelectric phenomenon can be represented by:

$$S = s^T T + dE$$

$$D = dT + \in^T E.$$

Herein, a denotes an elastic constant, d denotes a piezoelectric constant, and $\in$ denotes a dielectric constant.

When a short circuit is established between the top surface and the undersurface of the measurement specimen 2, and a stress T is applied under E=0, a strain S' is generated.

$$S'=s^E T$$

Herein, superscript E represents the condition that an electric field is constant (including zero). At this time, an electrical displacement D':

$$D'=dT''$$

is generated simultaneously in the measurement specimen 2.

In order to bring about an open circuit between the top surface and the undersurface and to make the electrical displacement D in the measurement specimen 2 zero while the stress T is held applied, it is necessary to add D' (= dT) adequate for canceling D having been generated in the reverse direction. At this time, another E' has been generated in the measurement specimen 2 because of D' and, therefore, this generates another strain S''.

$$E''=(1/\in^T)D''$$

$$S''=dE''=(d^2/\in^T)T$$

In sum, the strain S under D=0 can be represented as $$S=S'-S''=(s^E-d^2/\in_T)T^o \equiv s^D$$

Herein, $$s^D=(1-d^2/\in^T s^E)s^E$$

and, thereby, the electromechanical coupling constant k can be represented as $$k=d^2/\in^T s^E$$

$$s^D=(1-k^2)s^E$$

Consequently, the electromechanical coupling constant can be determined from the Young's modulus $s^E$ under the condition of being short-circuited and the Young's modulus $s^D$ under the condition of being open-circuit obtained by measurement.

According to the measurement results in the case where PZT+1 wt % Nb was used as a sample, the $s^E$ and $s^D$ were 18.4 GPa and 25.7 GPa, respectively. The k was determined by calculation from this and the result was 0.532.

Figure 4:
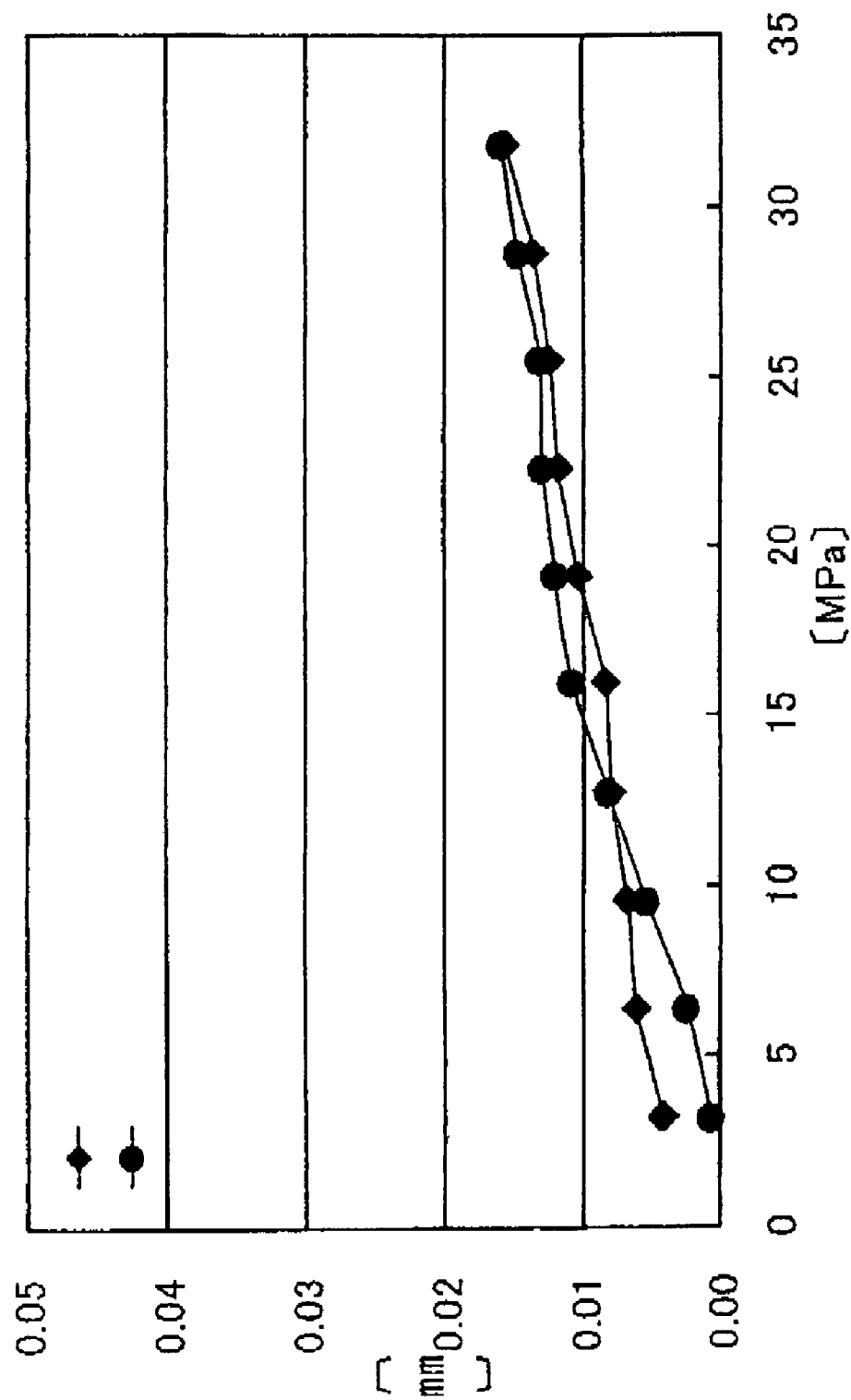
FIG. 4 is a graph showing a stress-displacement property of a sample.

FIG. 4 is a graph showing a stress-displacement property of a sample. As is clear from this result, although when the stress is 13 MPa or less, the displacement under the condition of being open-circuit is larger than the displacement under the condition of being short-circuited, when the stress becomes 13 MPa or more, the displacement under the condition of being short-circuited is larger than the displacement under the condition of being open-circuit.

What is claimed is:

1. A method for measuring a material property comprising the steps of stacking alternately three measurement specimens of the same material and the same dimension as each other, each having parallel planes, and two insertion plates of the same material and the same dimension as each other, each having known mechanical properties, applying a load to these measurement specimens and insertion plates via the measurement specimens located on both end sides, measuring the displacements in the direction of application of the load before and after application of the load, and determining an elastic constant of the measurement specimens based on those displacements.

2. The method for measuring a material property according to claim 1, wherein the displacements in the direction of application of the load before and after application of the load are measured as the displacements of the two insertion plates.

3. The method for measuring a material property according to claim 2, wherein the displacements of the two insertion plates are measured with laser displacement gauges which radiate laser light onto the top surface of the upper insertion plate and the undersurface of the lower insertion plate.

4. The method for measuring a material property according to any one of claims 1 to 3, wherein the measurement specimens are a bulky solid of a transducer which generates electric power based on application of mechanical energy.

5. The method for measuring a material property according to claim 4, further comprising the steps of measuring the elastic constants of the measurement specimen under the condition that the top surface and the undersurface of the measurement specimen located between the two insertion plates are electrically short-circuited and under the condition that no short-circuit is brought about, and determining the electromechanical coupling constant of the measurement specimens based on those elastic constants.

6. An apparatus for measuring a material property comprising two insertion plates of the same material and the same dimension as each other, each having known mechanical properties, to be stacked alternately with three measurement specimens of the same material and the same dimension as each other, each having parallel planes, a load application device for applying a load to these measurement specimens and insertion plates via the measurement specimens located on both end sides, and a displacement measurement device for measuring the displacement in the direction of application of the load before and after application of the load to these measurement specimens and insertion plates.

7. The apparatus for measuring a material property according to claim 6, wherein the displacement measurement device comprises devices which measure the displacements in the direction of application of the load as the displacements of the two insertion plates.

8. The apparatus for measuring a material property according to claim 7, wherein the displacement measurement devices for measuring the displacements of the two insertion plates are laser displacement gauges which measure the displacements by radiating laser light onto the top surface of the upper insertion plate and the undersurface of the lower insertion plate.

9. The apparatus for measuring a material property according to any one of claims 6 to 8, wherein a circuit for electrically connecting the top surface and the undersurface of the measurement specimen located between the two insertion plates is installed, and a make-and-break switch is installed in the circuit.

10. A method for measuring a material property of an alternating stack of three measurement specimens of the same material and the same dimension as each other, each having parallel planes, and two insertion plates of the same material and the same dimension as each other, each having known mechanical properties, comprising the steps of:

applying a load to these measurement specimens and insertion plates via the measurement specimens located on both end sides, measuring the displacements in the direction of application of the load before and after application of the load, determining an elastic constant of the measurement specimen based on those displacements, measuring the elastic constants of the measurement specimen under the condition that the top surface and the undersurface of the measurement specimen located between the two insertion plates are electrically short-circuited and under the condition that no short-circuit is brought about, and determining the electromechanical coupling constant of the measurement specimen based on those elastic constants.

11. An apparatus for measuring a material property of an alternating stack of three measurement specimens of the same material and the same dimension as each other, each having parallel planes, and two insertion plates of the same material and the same dimension as each other, each having known mechanical properties, comprising:

means for applying a load to these measurement specimens and insertion plates via the measurement specimens located on both end sides, means for measuring the displacements in the direction of application of the load before and after application of the load, means for determining an elastic constant of the measurement specimen based on those displacements, means for measuring the elastic constants of the measurement specimen under the condition that the top surface and the undersurface of the measurement specimen located between the two insertion plates are electrically short-circuited and under the condition that no short-circuit is brought about, and means for determining the electromechanical coupling constant of the measurement specimen based on those elastic constants.

* * * * *